(12) United States Patent
Son et al.

(10) Patent No.: US 8,652,986 B2
(45) Date of Patent: Feb. 18, 2014

(54) ZIEGLER-NATTA CATALYST FOR OLEFIN POLYMERIZATION

(75) Inventors: Ki Chul Son, Ansan-si (KR); Hyoung Lim Koh, Seoul (KR); Jin Kyu Ahn, Anyang-si (KR); Sang Hoon Lee, Seoul (KR)

(73) Assignee: Hyosung Corporation, Seoul (KR)

( * ) Notice: Subject to any disclaimer, the term of this patent is extended or adjusted under 35 U.S.C. 154(b) by 0 days.

(21) Appl. No.: 13/519,970

(22) PCT Filed: Dec. 29, 2010

(86) PCT No.: PCT/KR2010/009523
§ 371 (c)(1),
(2), (4) Date: Jun. 29, 2012

(87) PCT Pub. No.: WO2011/081460
PCT Pub. Date: Jul. 7, 2011

(65) Prior Publication Data
US 2012/0283089 A1    Nov. 8, 2012

(30) Foreign Application Priority Data

Dec. 31, 2009  (KR) .................. 10-2009-0135056
Dec. 31, 2009  (KR) .................. 10-2009-0135066
Nov. 3, 2010   (KR) .................. 10-2010-0108744

(51) Int. Cl.
| | | |
|---|---|---|
| C08F 4/42 | (2006.01) |
| C08F 4/76 | (2006.01) |
| C08F 4/58 | (2006.01) |
| C08F 4/78 | (2006.01) |
| C08F 4/649 | (2006.01) |
| C08F 4/44 | (2006.01) |
| C08F 4/72 | (2006.01) |

(52) U.S. Cl.
USPC .......... 502/154; 502/167; 502/168; 502/170; 502/169

(58) Field of Classification Search
None
See application file for complete search history.

(56) References Cited

U.S. PATENT DOCUMENTS

| | | |
|---|---|---|
| 4,532,313 A | 7/1985 | Matlack et al. |
| 4,654,318 A | 3/1987 | Yamamoto et al. |
| 4,952,649 A | 8/1990 | Kioka et al. |
| 5,476,825 A | 12/1995 | Fushimi et al. |
| 6,121,393 A | 9/2000 | Kioka et al. |
| 6,617,278 B1 | 9/2003 | Jin et al. |
| 6,841,633 B2 | 1/2005 | Bhaduri et al. |

FOREIGN PATENT DOCUMENTS

| | | |
|---|---|---|
| CN | 1041764 | 5/1990 |
| CN | 1174206 | 2/1998 |
| CN | 1257879 | 6/2000 |
| CN | 1298888 | 6/2001 |
| JP | 57-070105 A | 4/1982 |
| JP | 58-083006 A | 5/1983 |
| JP | 62-007706 A | 1/1987 |
| JP | 06-025340 A | 2/1994 |
| JP | 09-052909 A | 2/1997 |
| KR | 10-1991-0008283 B1 | 10/1991 |
| KR | 10-10-0417257 B1 | 2/2004 |

OTHER PUBLICATIONS

PCT International Search Report and Written Opinion of the International Searching Authority, PCT/KR2010/009523, Sep. 16, 2011, 5 Pages.

*Primary Examiner* — Yun Qian
(74) *Attorney, Agent, or Firm* — Fenwick & West LLP

(57) ABSTRACT

The present invention relates to a Ziegler-Natta catalyst, and more specifically to a Ziegler-Natta catalyst for olefin polymerization which may use a compound of Formula 3 as an internal electron donor to obtain polymers with high activity, wide molecular weight distribution and low content of fine particle.

1 Claim, No Drawings

ZIEGLER-NATTA CATALYST FOR OLEFIN POLYMERIZATION

DESCRIPTION

1. Technical Field

The present invention relates to a Ziegler-Natta catalyst, and more specifically to a Ziegler-Natta catalyst for olefin polymerization which may use a compound of Formula 3 as an internal electron donor to obtain polymers with high activity, wide molecular weight distribution and low content of fine particles.

2. Background Art

A catalyst for olefin polymerization, which is generally called a Ziegler-Natta catalyst, refers to a catalyst system consisting of combinations of a main catalyst containing a transition metal compound as a main component, a promoter which is an organic metal compound and an electronic donor, and studies have been widely conducted for improving polymerization activity and isotacticity index, widening the molecular weight distribution of polymers or reducing fine particle contents of polymers in the related art and as a result, a great deal of related technologies have been suggested.

Ziegler-Natta catalysts have direct effects on properties and characteristics and the like of polyolefins produced depending on components and preparation methods thereof. Thus, in order to modify the characteristics of produced polyolefins produced, a change in components of a catalyst, a change in structure of a carrier, a change in method for preparing a catalyst and the like need to be achieved, and studies on the activity of a catalyst, the molecular weight of a polymer obtained, the isotacticity index and the like need to be conducted together.

Ziegler-Natta catalysts in the related art consist of a system of solid catalyst components containing titanium, magnesium and halogen as main components and an aluminum compound as a promoter. In the system, in order to improve catalytic activity and isotacticity index as main elements, a great deal of improvements have been made, but due to diversified use of polyolefins, catalytic activity, isotacticity index, wide molecular weight distribution or distribution of low content of fine particles have been additionally required for the present purpose.

In order to solve the isotacticity index problem, methods for adding an electron donor are described in U.S. Pat. No. 4,544,717 and high isotacticity index catalysts with a value of between 94 and 95 or more in isotacticity index are described in U.S. Pat. No. 4,226,741. Further, in EP No. 045,977, a technology of a solid Ziegler-Natta catalyst with characteristics of high activity and high isotacticity index is described, and derivatives of a specific carboxylic acid ester compound and preferably phthalate derivatives are coordinated to a solid catalyst compound as an internal electron donor to prepare a Ziegler-Natta catalyst along with a titanium compound. In addition, there have been suggested methods that these main catalysts may enhance polymerization activity and isotacticity index by alpha-olefin polymerization using an aluminum alkyl compound and a silicon compound having at least one silicon-ether bonds as an external electron donor by alpha-olefin polymerization using an aluminum alkyl compound and a silicon compound having at least one silicon-ether bonds as an external electron donor, and the like. However, in the case of these preparation methods, some methods have difficulty in controlling the size of carrier particles and the molecular weight distribution of polymers are not good in some cases.

Further, in order to widen the molecular weight distribution, in International Publication No. WO 00/63261 a method for widening the isotacticity index and molecular weight distribution by using succinate derivatives as an internal electron donor in the solid catalyst components instead of phthalate is suggested. However, during the polymerization, there is a problem in that the catalytic activity has rapidly deteriorated during the polymerization process and thus current requirements have not been satisfied.

In addition, in order to reduce the fine particle content of a polymer by making the particle size uniform, in US Published Application Nos. U.S. Pat. Nos. 4,946,816, 4,866,022, 4,988,656 and 5,124,297, there have been methods, including: (i) preparing a solution containing magnesium from a magnesium compound in the presence of alcohol, (ii) precipitating the magnesium solution in the presence of a transition metal halide or an organic silane additive, and (iii) reacting an electron donor compound with transition metal components in the precipitate to prepare a catalyst with uniform particle size. However, these methods are disadvantageous in that there are many catalyst preparation steps, preparation processes are complicated, the catalytic activity has rapidly deteriorated during polymerization process, and an obtained catalyst contains large amounts of fine particles due to problems relating to isotacticity index or particle size of a polymer.

Thus, there is a need for developing a new Ziegler-Natta catalyst for olefin polymerization, which may be obtained by a relatively simple catalyst preparation method, has high polymerization activity, isotacticity index, and by which polymers with wide molecular weight distribution and low fine particle content may be obtained.

DETAILED DESCRIPTION OF THE INVENTION

[Technical Problem]

The present invention have intensively studied Ziegler-Natta catalysts for olefin polymerization with high activity, high isotacticity index, wide molecular weight distribution and low fine particle content and found that when a compound of Formula 3 as an internal electron donor used during the preparation of Ziegler-Natta catalysts, in particular, amide, carboxylic acid anhydride or acyl sulfide is used, a solid catalyst prepared exhibits high activity and in the case of polyolefins prepared by using the solid catalyst in olefin polymerization reactions, a polymer thus produced has high isotacticity index, wide molecular weight distribution and low fine particle content, thereby completing the present invention.

An object of the present invention is to provide a Ziegler-Natta catalyst for olefin polymerization which may obtain polymers with high activity, high isotacticity index, wide molecular weight distribution, and low fine particle content.

[Technical Solution]

A Ziegler-Natta catalyst for olefin polymerization according to the present invention is characterized in that a compound with a structure of Formula 3 is used as an internal electron donor.

Formula 3

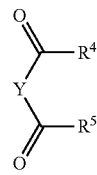

where, Y is any one of N—R$^3$, O or S,

R$^3$, R$^4$ and R$^5$ may be the same as or different from each other and are hydrogen or C$_1$ to C$_{20}$ linear or branched alkyl, alkenyl, cycloalkyl, aryl, aryl alkyl, an aryl substitution product, alkyl aryl, an alkyl aryl substitution product or alkyl aryl including a heteroatom.

Further, the present invention is characterized by using amide, a carboxylic acid anhydride and diacyl sulfide as an internal electron donor, in the process of preparing a Ziegler-Natta catalyst for olefin polymerization obtained in the process, including: (a) dissolving anhydrous magnesium halide in anhydrous alcohol and a hydrocarbon solvent and then adding a precipitation promoter thereto to prepare a magnesium carrier mixture solution, (b) adding the magnesium carrier mixture solution to a transition metal compound and reacting the resulting mixture to obtain a precipitate, and (c) washing the precipitate with a hydrocarbon solvent, adding a transition metal compound thereto, and then washing the resulting mixture with a hydrocarbon solvent until a titanium component is not detected.

According to other preferred characteristics of the present invention, the internal electron donor is added in any one or more of step (a) to step (c).

The Ziegler-Natta catalyst prepared by the present invention is characterized in that 0.1 wt % to 6.0 wt % of titanium, 10 wt % to 30 wt % of magnesium, 40 wt % to 70 wt % of halogen and 5 wt % to 30 wt % of an internal electron donor are included based on the total weight of the catalyst.

[Advantageous Effects]

The Ziegler-Natta catalyst for olefin polymerization according to the present invention exhibits high activity and high isotacticity index, and thus the used amount of titanium, which is expensive among the raw materials may be greatly reduced, thereby leading to reduction in costs of preparing the catalyst. Furthermore, polyolefins prepared by using the Ziegler-Natta catalyst of the present invention may be useful in molding materials such as plates, films, containers, fabrics and the like due to wide molecular weight distribution and low fine particle content.

[Best Mode]

A Ziegler-Natta catalyst for olefin polymerization is obtained by the following process.

(a) Dissolving anhydrous magnesium halide in anhydrous alcohol and a hydrocarbon solvent, and adding a precipitation promoter thereto to prepare magnesium carrier mixture solution, (b) Adding the magnesium carrier mixture to a transition metal compound and reacting the resulting mixture to obtain a precipitate, and (c) Washing the precipitate with a hydrocarbon solvent, adding a transition metal compound thereto, and then washing the resulting mixture with a hydrocarbon solvent until a titanium component is not detected, thereby obtaining a solid catalyst.

The present invention is characterized by using a compound with a structure of Formula 3 as an internal electron donor used in the process of preparing a solid catalyst component of the above-described Ziegler-Natta catalyst for olefin polymerization, in particular, diacyl sulfide, carboxylic acid anhydride or amide and adding the internal electron donor herein represented by Formula 3 in step (a), step (c) or steps (a) and (c).

Formula 3

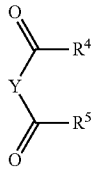

where, Y is any one of N—$R_3$, O or S, $R_3$, $R_4$ and $R_5$ may be the same as or different from each other, hydrogen or $C_1$ to $C_{20}$ linear or branched alkyl, alkenyl, cycloalkyl, aryl, aryl alkyl, an aryl substitution product, alkyl aryl, an alkyl aryl substitution product or alkyl aryl including a heteroatom.

Specifically, when Y is N—$R_3$, the compound of Formula 3 is an amide, and examples of the amide include N-benzoyl-N-methylbenzamide, N-benzoyl-N-ethylbenzamide, N-benzoyl-N-propylbenzamide, N-benzoyl-N-isopropylbenzamide, N-benzoyl-N-butylbenzamide, N-benzoyl-N-hexylbenzamide, N-benzoyl-N-cylcopentylbenzamide, N-benzoyl-N-cyclohexylbenzamide, N-benzoyl-N-phenylbenzamide, N-propionyl-N-methylbenzamide, N-propionyl-N-ethylbenzamide, N-propionyl-N-propylbenzamide, N-propionyl-N-isopropylbenzamide, N-propionyl-N-butylbenzamide, N-propionyl-N-hexylbenzamide, N-propionyl-N-cyclopentylbenzamide, N-propionyl-N-cyclohexylbenzamide, N-propionyl-N-methylbenzamide, N-butyryl-N-ethylbenzamide, N-butyryl-N-propylbenzamide, N-butyryl-N-isopropylbenzamide, N-butyryl-N-butylbenzamide, N-butyryl-N-hexylbenzamide, N-butyryl-N-cyclopentylbenzamide or N-butyryl-N-cyclohexylbenzamide.

Further, when Y is 0, the compound of Formula 3 is a carboxylic acid anhydride, and examples of the carboxylic acid anhydride may include carboxylic acid anhydride compounds and the like, such as acetic anhydride, propionic anhydride, n-butyric anhydride, isobutyric anhydride, palmitic anhydride, heptanoic anhydride, hexanoic anhydride, stearic anhydride, nonanoic anhydride, 2-ethylhexanoic anhydride, 2-sulfobenzoic anhydride, 1,8-naphthalic anhydride, phthalic anhydride, 1,2,4,5-benznetetracarboxylic anhydride, benzoic anhydride, glycine anhydride, succinic anhydride, maleic anhydride, glutaric anhydride, tetrachlorophthalic anhydride, 3-methylphthalic anhydride, 3-chlorophthalic anhydride, isatoic anhydride, carbic anhydride, 3-fluorophthalic anhydride, 4-fluorophthalic anhydride, 4-methylphthalic anhydride, trifluorophthalic anhydride, tetrafluorophthalic anhydride, chloroacetic anhydride, citraconic anhydride, tetrabromophthalic anhydride, 2,3-pyridinedicarboxylic anhydride, homophthalic anhydride, cis-1,2,3,6-tetrahydrophthalic anhydride, 4,5-dichlorophthalic anhydride, trimethylacetic anhydride, itaconic anhydride, 3,4,5,6-tetrahydrophthalic anhddydride, 2,2-dimethylglutaric anhydride, 3,3-dimethylglutaric anhydride, 2-phenylglutaric anhydride, dichloroacetic anhydride, 3-methylglutaric anhydride, diglucolic anhydride, 2,3-pyrazinedicarboxylic anhydride, 3,3-tetramethyleneglutaric anhydride, diphenic anhydride, 3-ethyl-3-methylglutaric anhydride, isonicotinic anhydride, cis-1,2-cyclohexanedicarboxylic anhydride, 2,2-dimethylsuccinic anhydride, hexahydro-4-methylphthalic anhydride, 3-hydroxyphthalic anhydride, iodoacetic anhydride and the like.

In addition, when Y is S, the compound of Formula 3 is a diacyl sulfide, and examples of the diacyl sulfide may include diacyl sulfide compounds such as dibenzoyl sulfide, bis(2-methylbenzoyl)sulfide), bis(3-methylbenzoyl)sulfide, bis(4-methylbenzoyl)sulfide, bis(4-methoxybenzoyl)sulfide, bis(4-chlorobenzoyl)sulfide, bis(4-nitrobenzoyl)sulfide, dipropionyl sulfide, dibutyryl sulfide, bis(2-methylpropionyl)sulfide, bis(3-methylpropionyl)sulfide, bis(4-methylpropionyl)sulfide, di-n-hexanoyl sulfide, distearoyl sulfide, bis(phenoxyacetyl)sulfide and the like.

Hereinafter, each step will be described with reference to specific examples.

Step (a) is a step of dissolving anhydrous magnesium halide in anhydrous alcohol and a hydrocarbon solvent, adding a precipitation promoter thereto, and reacting the resulting mixture at 60° C. to 150° C. for 1 to 5 hr to prepare a magnesium carrier mixture solution.

That is, step (a) is a step of preparing a magnesium carrier mixture solution, in which 1 mole of anhydrous magnesium dichloride is dissolved in 0.1 mole to 20 mole, preferably 0.1 mole to 10 mole of anhydrous alcohol and 0.1 mole to 20 mole of a hydrocarbon solvent, 0.001 mole to 10 mole, preferably 0.001 mole to 1 mole of a precipitation promoter is added thereto, and the resulting mixture is reacted at 60° C. to 150° C. for 1 hr to 5 hr to prepare a magnesium carrier mixture solution.

The hydrocarbon solvent may include an aliphatic hydrocarbon such as isobutene, pentane, hexane, heptane, octane, nonane, decane, dodecane, hexadecane, octadecane and the like; an alicyclic hydrocarbon such as cyclopentane, methyl cyclopentane, cyclohexane, cyclooctane and the like; and an aromatic hydrocarbon such as benzene, toluene, xylene and the like, preferably an aliphatic hydrocarbon, and more preferably decane.

The precipitation promoter serves to control the rate of producing catalyst particles, and may include anhydrous organic acids such anhydrous acetic acid, anhydrous phthalic acid, anhydrous succinic acid, anhydrous maleic acid, anhydrous succinic acid and the like; organic acids such as acetic acid, propionic acid, butyric acid, acrylic acid, methacrylic acid and the like; ketones such as acetone, methyl ethyl ketone, benzophenone and the like; ethers such as dimethyl ether, diethyl ether, dipropyl ether, dibutyl ether, diamyl ether, 1,3-diether and the like, aldehyde, succinate, diacyl sulfide, amide and mixtures thereof, preferably anhydrous organic acid, and more preferably anhydrous phthalic acid. The concentration of the precipitation promoter is 0.01 mole to 10 mole per mole of anhydrous magnesium dichloride and preferably 0.01 mole to 1 mole.

Herein, the anhydrous magnesium halide has a structure of Formula 1, and it is preferred that anhydrous magnesium dichloride ($MgCl_2$) is particularly used.

$MgX_n(OR1)4-n$ 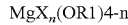 Formula 1

In Formula 1, M is a metal, X is a halogen, $R_1$ is $C_1$ to $C_{10}$ hydrocarbyloxy, and n is 0 to 2 as an oxidation number of the metal.

Preferably, X is Cl, Br and I and $R_1$ is $C_1$ to $C_4$ alkoxy or phenoxy.

More preferably, in Formula 1, X is Cl and $R_1$ is ethoxy or butoxy. Most preferably, in Formula 1, X is Cl.

Step (b) is a step of obtaining a precipitate of a solid catalyst, in which 1 mole of 20 mole of the transition metal compound represented by Formula 2 per mole of magnesium and a hydrocarbon solvent are cooled to −40° C. to 10° C., a magnesium carrier mixture is slowly added dropwise thereto for 1 hr to 5 hr, the temperature is heated at a rate of 0.1 ml/min to 5 ml/min at 70° C. to 130° C. for 1 hr to 6 hr, and then the resulting mixture is reacted for 1 hr to 4 hr to obtain a precipitate. At this time, the temperature condition and the heating rate have effects on the uniformity of a support.

$MXn(OR2)4-n$  Formula 2

In Formula 2, M is a metal, X is a halogen, R2 is $C_1$ to $C_{10}$ hydrocarbyloxy, and n is 0 to 4 as an oxidation number of the metal.

Preferably, in Formula 2, M is a Group IVB metal such as Ti, Zr, Hf, Rf and the like; a Group VB metal such as V, Nb, Ta, Db and the like; or a Group VB metal such as Cr, Mo, W, Sg and the like.

X is Cl, Br and I, and $R_2$ is $C_1$ to $C_4$ alkoxy or phenoxy.

More preferably, in Formula 2, M is a Group IVB metal such as Ti, Zr, Hf, Rf and the like, X is Cl, and R1 is ethoxy or butoxy. Most preferably, in Formula 2, M is Ti and $R_2$ is Cl.

In step (c), a solid catalyst precipitate is washed with a hydrocarbon solvent, 1 mole to 20 mole of a transition metal compound and 0.01 mole to 2 mole of an internal electron donor per mole of magnesium are added thereto at 50° C. to 130° C., the resulting mixture is reacted for 1 hr to 5 hr, and solid components are filtered, thereby obtaining a compound. The compound prepared is washed with a hydrocarbon solvent until a titanium component is not detected, thereby obtaining a solid catalyst.

Herein, it is described that an internal electron donor is added in step (c), but the internal electron donor is not always added in step (c), and may be added together with a precipitation promoter in step (c). Furthermore, the internal electron donor may be added simultaneously in steps (a) and (c).

Components of the solid catalyst prepared by the method include 0.1 wt % weight to 6.0 wt % of titanium, 10 wt % to 30 wt % of magnesium, 40wt % to 70wt % of halogen and 5 wt % to 30 wt % of an internal electron donor based on the total weight of the catalyst. Further, the solid catalyst prepared exhibits high activity, high isotacticity index, wide molecular weight distribution and low content of fine particles, and in order to improve the catalytic activity, it is preferred that the catalyst is prepared with a transition metal compound supported on a carrier.

When the solid catalyst prepared is applied to the polymerization of olefins, the catalyst prepared, an organic aluminum compound represented by the following Formula 4 and an external electron donor represented by the following Formula 5 are used as a main catalyst, a promoter and a co-catalyst, respectively.

$R^6{}_n AlX_{3-n}$  Formula 4

In Formula 4, $R^6$ is $C_1$ to $C_{20}$ alkyl, X is a halogen, and n is 0 to 3.

$R^7{}_n Si(OR^8)_{4-n}$ 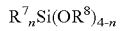 Formula 5

In Formula 5, R7 is a $C_1$ to $C_{20}$ hydrocarbon and preferably $C_1$ to $C_{10}$ alkyl, $C_5$ to $C_{12}$ cycloalkyl, $C_6$ to $C_{20}$ aryl, $C_1$ to $C_{10}$ alkenyl, $C_1$ to $C_{10}$ haloalkyl or $C_1$ to $C_{10}$ aminoalkyl and chlorine, and $R^8$ is a $C_1$ to $C_{20}$ hydrocarbon and preferably $C_1$ to $C_{10}$ alkyl, $C_5$ to $C_{12}$ cycloalkyl, $C_6$ to $C_{20}$ aryl, $C_1$ to $C_{10}$ alkenyl and $C_2$ to $C_{10}$ alkoxyalkyl, and n is 0 to 4.

The compound represented by Formula 5 is preferably an organic silicon compound, and specific examples thereof include triethyl methoxysilane, trimethyl ethoxysilane, dimethyl dimethoxysilane, dimethyl dimethoxysilane, diisopropyl dimethoxysilane, diphenyl dimethoxysilane, phenylmethyl dimethosysilane, diphenyl diethoxysilane, dicyclohexyl dimethoxysilane, cyclohexylmethyl dimethoxysilane, cyclohexylmethyl diethoxysilane, dicyclopentyl dimethoxysilane, dicyclopentyl diethoxysilane, ethyl trimethoxysilane, ethyl triethoxysilane, vinyl trimethoxysilane, and vinyl triethoxysilane, and preferably diphenyl dimethoxysilane, cyclohexylmethyl dimethoxysilane and dicyclopentyl diethoxysilane.

The external electron donor is used together with a promoter during polymerization, and may be used if necessary. The concentration of the external electron donor is from 0.001% by mole to 50% by mole, preferably from 0.01% by mole to 20% by mole and more preferably 0.02% by mole to 10% by mole, per mole of the promoter. When the concentration of the external electron donor is less than 0.001% by mole, a problem that improvement in isotacticity index is not achieved occurs. When the concentration exceeds 50% by mole, the isotacticity index is no longer affected.

When the solid catalyst according to the present invention is applied to the polymerization of olefins, polyolefins with high isotacticity index, high activity and wide molecular weight distribution may be prepared.

An olefin for polymerization is $CH_2=CHR$, where R is H or $C_1$ to $C_{12}$.

In the present invention, "polymerization" includes single polymerization and copolymerization.

The polymerization reaction may be performed in a vapor phase, a liquid phase or a solution phase. When the polymerization reaction is performed in a liquid phase, a hydrocarbon solvent may be used, and olefin itself may also be used as a solvent. The polymerization temperature is usually from $-50°$ C. to 350° C. and preferably from 0° C. to 200° C. When the polymerization temperature is less than $-50°$ C., the activity of the catalyst deteriorates. When the polymerization temperature exceeds 350° C., the isotacticity index deteriorates, which is not suitable. The polymerization pressure is usually from normal pressure to 250 atm and preferably from normal pressure to 200 atm, and the polymerization reaction may be performed by any method of a batch type, a semi-continuous type and a continuous type. When the polymerization pressure is 250 atm or more, the pressure is not preferred industrially and economically.

To the polyolefin prepared by using the solid catalyst according to the present invention, a heat stabilizer, a light stabilizer, a flame retardant, carbon black, a pigment, an antioxidant and the like may be added. In addition, the polyolefin as prepared above may be mixed with low density polyethylene (LDPE), high density polyethylene (HDPE), polypropylene, polybutene, ethylene/propylene (EP) rubber and the like and the mixture may be used.

The Ziegler-Natta catalyst for olefin polymerization according to the present invention exhibits high activity and high isotacticity index, and thus the used amount of titanium, which is expensive among the raw materials may be greatly reduced, thereby leading to reduction in costs of preparing the catalyst. Furthermore, polyolefins prepared by using the Ziegler-Natta catalyst of the present invention may be useful in molding materials such as plates, films, containers, fabrics and the like because particles are large and uniform and exhibit wide molecular weight distribution.

Hereinafter, preferred Examples will be suggested for better understanding of the present invention. However, the following Examples are provided only for the purpose of illustrating the present invention, and thus the present invention is not limited thereto.

EXAMPLES AND COMPARATIVE EXAMPLES

Catalyst Performance Evaluation Experiment

In order to evaluate the performance of the Ziegler-Natta catalyst according to the present invention, an experiment was performed in the following manner.

Propylene was polymerized by using a 2-liter polymerization reactor. Pressure in the reactor was reduced to a vacuum of 3 Torr or less, and a process of filling the reactor with high purity nitrogen was repeated five times. The reactor was filled with 500 g of propylene and 750 cc of hydrogen at normal temperature, 3 mmol of triethyl aluminum, 0.18 mmol of dicyclopentyl dimethoxysilane and 0.0044 mmol of the catalyst prepared in each of the following Examples and Comparative Examples were introduced into the reactor, then the temperature of the reactor was increased to 70° C., and a reaction was performed for 1 hr. A small amount of methanol was introduced into the polymer to complete the polymerization. A reaction product was mixed with about 5wt % by weight of HCl-methanol and the mixture was stirred for 24 hr, and then the resulting mixture was stirred in pure methanol for 24 hr, washed, filtered with a filter paper, and then dried under vacuum at about 80° C. for 12 hr or more to obtain a final polymerization product.

The activity of the catalyst was obtained as a unit of kg-polymer/g-catalyst from the weight of the final polymerization product.

The isotacticity index (I.I.) of polypropylene was obtained as an isotacticity index, which is an amount at which polypropylene is not dissolved in boiling heptane. The polymer had been previously treated with a heat stabilizer to prevent decomposition during the analysis. A predetermined amount of a completely dried polymer was exactly measured and placed in a timble filter, and then was extracted with heptane in a Soxhlet type extracting device. The extraction time was fixed as 5 hours, residual polymer which had not been dissolved after the extraction was collected and dried at 80° C. under vacuum, and then the weight of the residual polymer was measured and the isotacticity index was obtained by using a weight ratio of the weight of the residual polymer which had not been dissolved and the weight of the polymer which had been originally introduced.

Example 1

Under the atmosphere of high purity nitrogen, 4.8 g (0.05 mol) of anhydrous magnesium dichloride, 25 ml (0.16 mol) of 2-ethyl-1-hexanol and 23 ml (0.12 mol) of decane were placed in a double-jacketed glass reactor equipped with a stirrer, the temperature was increased to 130° C., and then the mixture was stirred until a clear solution was produced. 1.4 g (0.01 mol) of anhydrous phthalic acid was added thereto and the mixture was stirred for 1 hr to prepare a magnesium carrier mixture solution. The temperature was decreased to $-20°$ C., 14 ml (0.1 mol) of titanium tetrachloride and 100 ml (0.94 mol) of toluene were slowly added dropwise to the magnesium carrier mixture solution, the temperature was constantly increased up to 110° C. at a rate of 0.5 ml/min, and then the mixture was maintained at the temperature for 2 hr to obtain a compound. The compound was washed twice with toluene, 25 ml (0.23 mol) of titanium tetrachloride and 100 ml (0.94 mol) of toluene were added thereto, the temperature was increased up to 110° C., 2.4 g (0.010 mol) of dibenzoyl sulfide was added thereto, and the reaction was performed for 2 hr to obtain a precipitate. Thereafter, solid components were filtered and washed with toluene and hexane to obtain a solid catalyst.

Example 2

A solid catalyst was prepared in the same manner as in Example 1, except that 2.7 g (0.01 mol) of bis(2-methylbenzoyl)sulfide was used instead of dibenzoyl sulfide in Example 1.

Example 3

A solid catalyst was prepared in the same manner as in Example 1, except that 2.7 g (0.05 mol) of bis(3-methylbenzoyl)sulfide was used instead of dibenzoyl sulfide in Example 1.

Example 4

A solid catalyst was prepared in the same manner as in Example 1, except that 2.7 g (0.05 mol) of bis(4-methylbenzoyl)sulfide was used instead of dibenzoyl sulfide in Example 1.

Example 5

A solid catalyst was prepared in the same manner as in Example 1, except that 3.0 g (0.01 mol) of bis(4-methoxybenzoyl)sulfide was used instead of dibenzoyl sulfide in Example 1.

Example 6

A solid catalyst was prepared in the same manner as in Example 1, except that 3.1 g (0.01 mol) of bis(4-chlorobenzoyl)sulfide was used instead of dibenzoyl sulfide in Example 1.

Example 7

A solid catalyst was prepared in the same manner as in Example 1, except that 3.3 g (0.01 mol) of bis(4-nitrobenzoyl)sulfide was used instead of dibenzoyl sulfide in Example 1.

Example 8

A solid catalyst was prepared in the same manner as in Example 1, except that 1.5 g (0.01 mol) of dipropionyl sulfide was used instead of dibenzoyl sulfide in Example 1.

Example 9

A solid catalyst was prepared in the same manner as in Example 1, except that 1.7 g (0.01 mol) of dibutyryl sulfide was used instead of dibenzoyl sulfide in Example 1.

Example 10

A solid catalyst was prepared in the same manner as in Example 1, except that 1.7 g (0.01 mol) of bis(2-methylpropionyl)sulfide was used instead of dibenzoyl sulfide in Example 1.

Example 11

A solid catalyst was prepared in the same manner as in Example 1, except that 2.3 g (0.01 mol) of di-n-hexanoyl sulfide was used instead of dibenzoyl sulfide in Example 1.

Example 12

A solid catalyst was prepared in the same manner as in Example 1, except that 5.7 g (0.01 mol) of distearoyl sulfide was used instead of dibenzoyl sulfide in Example 1.

Example 13

A solid catalyst was prepared in the same manner as in Example 1, except that 3.0 g (0.01 mol) of bis(phenoxyacetyl)sulfide was used instead of dibenzoyl sulfide in Example 1.

Example 14

A solid catalyst was prepared in the same manner as in Example 1, except that 1.6 g (0.010 mol) of butyric anhydride was used instead of dibenzoyl sulfide in Example 14.

Example 15

A solid catalyst was prepared in the same manner as in Example 1, except that 2.3 g (0.01 mol) of benzoic anhydride was used instead of dibenzoyl sulfide in Example 14.

Example 16

A solid catalyst was prepared in the same manner as in Example 1, except that 1.0 g (0.01 mol) of acetic anhydride was used instead of dibenzoyl sulfide in Example 14.

Example 17

A solid catalyst was prepared in the same manner as in Example 1, except that 1.6 g (0.01 mol) of isobutyric anhydride was used instead of dibenzoyl sulfide in Example 14.

Example 18

A solid catalyst was prepared in the same manner as in Example 1, except that 2.5 g (0.01 mol) of N-benzoyl-N-methylbenzamide was used instead of dibenzoyl sulfide in Example 1.

Example 19

A solid catalyst was prepared in the same manner as in Example 1, except that 2.5 g (0.01 mol) of N-benzoyl-N-ethylbenzamide was used instead of dibenzoyl sulfide in Example 1.

Example 20

A solid catalyst was prepared in the same manner as in Example 1, except that 2.7 g (0.01 mol) of N-benzoyl-N-propylbenzamide was used instead of dibenzoyl sulfide in Example 1.

Example 21

A solid catalyst was prepared in the same manner as in Example 1, except that 3.0 g (0.01 mol) of N-benzoyl-N-phenylbenzamide was used instead of dibenzoyl sulfide in Example 1.

Comparative Example 1

A solid catalyst was prepared in the same manner as in Example 1, except that 2.2 g (0.01 mol) of diethyl phthalate was used instead of dibenzoyl sulfide in Example 1.

Comparative Example 2

A solid catalyst was prepared in the same manner as in Example 1, except that 2.8 g (0.01 mol) of diisobutyl phthalate was used instead of dibenzoyl sulfide in Example 1.

The polymerization activity of the catalyst and the isotacticity index and characteristics of the polymerization product are shown in Table 1.

TABLE 1

|  | Ti content (wt %) | Activity (kg/g cat) | Isotacticity index (%) | Average particle diameter (μm) | Distribution of fine particles of polymer | Molecular weight distribution (MWD) |
|---|---|---|---|---|---|---|
| Example 1 | 1.9 | 44.5 | 98.5 | 470 | 0.5 | 5.8 |
| Example 2 | 1.4 | 41.0 | 97.9 | 460 | 0.2 | 5.2 |
| Example 3 | 1.6 | 40.5 | 98.2 | 465 | 0.6 | 5.3 |
| Example 4 | 1.5 | 45.0 | 98.1 | 480 | 0.1 | 5.4 |
| Example 5 | 1.8 | 46.5 | 97.9 | 485 | 0.3 | 5.0 |
| Example 6 | 1.6 | 38.0 | 97.8 | 466 | 0.4 | 4.9 |
| Example 7 | 1.5 | 41.0 | 98.1 | 485 | 0.1 | 5.4 |
| Example 8 | 1.7 | 36.0 | 98.0 | 476 | 0.2 | 5.1 |
| Example 9 | 1.6 | 38.0 | 98.2 | 483 | 0.7 | 5.3 |
| Example 10 | 1.5 | 35.5 | 97.9 | 450 | 1.0 | 5.2 |
| Example 11 | 1.7 | 37.0 | 97.8 | 460 | 1.6 | 5.1 |
| Example 12 | 1.6 | 38.0 | 98.0 | 470 | 0.5 | 5.5 |
| Example 13 | 1.8 | 43.5 | 98.0 | 486 | 0.4 | 5.4 |
| Example 14 | 1.2 | 33.5 | 98.0 | 520 | 0.1 | 4.1 |
| Example 15 | 1.6 | 34.5 | 98.1 | 490 | 0.2 | 4.2 |
| Example 16 | 2.5 | 24.0 | 98.0 | 485 | 0.2 | 4.7 |
| Example 17 | 0.8 | 27.0 | 98.2 | 510 | 0.1 | 5.0 |
| Example 18 | 1.0 | 28.0 | 98.0 | 478 | 0.6 | 4.9 |
| Example 19 | 1.4 | 32.0 | 97.9 | 476 | 0.1 | 5.2 |
| Example 20 | 1.2 | 33.0 | 98.1 | 505 | 0.3 | 5.3 |
| Example 21 | 1.3 | 35.0 | 98.3 | 500 | 0.2 | 5.6 |
| Comparative Example 1 | 2.5 | 20.0 | 97.7 | 460 | 2.1 | 4.4 |
| Comparative Example 2 | 0.8 | 25.0 | 97.5 | 480 | 0.9 | 4.8 |

As shown in Table 1, it was confirmed that the Ziegler-Natta catalyst with a structure of Formula 3, using amide, carboxylic acid anhydride and diacyl sulfide as an internal electron donor according to the present invention, exhibits high activity, high isotacticity index and low content of fine particle.

The invention claimed is:

1. A Ziegler-Natta catalyst for olefin polymerization comprising an internal electron donor an amide compound:

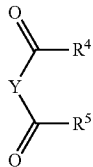

selected from the group consisting of N-benzoyl-N-methylbenzamide, N-benzoyl-N-ethylbenzamide, N-benzoyl-N-propylbenzamide, N-benzoyl-N-isopropylbenzamide, N-benzoyl-N-butylbenzamide, N-benzoyl-N-hexylbenzamide, N-benzoyl-N-cylcopentylbenzamide, N-benzoyl-N-cyclohexylbenzamide, N-benzoyl-N-phenylbenzamide, N-propionyl-N-methylbenzamide, N-propionyl-N-ethylbenzamide, N-propionyl-N-propylbenzamide, N-propionyl-N-isopropylbenzamide, N-propionyl-N-butylbenzamide, N-propionyl-N-hexylbenzamide, N-propionyl-N-cyclopentylbenzamide, N-propionyl-N-cyclohexylbenzamide, N-propionyl-N-methylbenzamide, N-butyryl-N-ethylbenzamide, N-butyryl-N-propylbenzamide, N-butyryl-N-isopropylbenzamide, N-butyryl-N-butylbenzamide, N-butyryl-N-hexylbenzamide, N-butyryl-N-cyclopentylbenzamide and N-butyryl-N-cyclohexylbenzamide.

* * * * *